United States Patent [19]

Kaplan et al.

[11] Patent Number: 4,542,253
[45] Date of Patent: Sep. 17, 1985

[54] USE OF PHOSPHATE AND THIOPHOSPHATE ESTERS NEUTRALIZED WITH WATER SOLUBLE AMINES AS ETHYLENE FURNACE ANTI-COKING ANTIFOULANTS

[75] Inventors: Morris Kaplan, Houston; William A. Lindley, Sugar Land, both of Tex.

[73] Assignee: Nalco Chemical Company, Oak Brook, Ill.

[21] Appl. No.: 607,052

[22] Filed: May 4, 1984

Related U.S. Application Data

[63] Continuation-in-part of Ser. No. 522,292, Aug. 11, 1983, abandoned, which is a continuation-in-part of Ser. No. 410,218, Aug. 23, 1982, abandoned.

[51] Int. Cl.$^4$ .................. C07C 11/04; C10G 9/16
[52] U.S. Cl. ..................... 585/650; 585/648; 585/950; 208/47; 208/48 AA
[58] Field of Search .......... 585/648, 650, 950; 208/47, 48 AA

[56] References Cited

U.S. PATENT DOCUMENTS

| | | | |
|---|---|---|---|
| 4,024,048 | 5/1977 | Shell et al. | 208/48 AA |
| 4,024,049 | 5/1977 | Shell et al. | 208/48 AA |
| 4,024,050 | 5/1977 | Shell et al. | 208/48 AA |
| 4,024,051 | 5/1977 | Shell et al. | 208/48 AA |
| 4,105,540 | 8/1978 | Weinland | 208/48 AA |
| 4,106,904 | 8/1978 | Oudeauuke et al. | 208/47 |
| 4,154,779 | 5/1979 | Kreutzer | 260/924 |
| 4,229,284 | 10/1980 | White et al. | 208/47 |
| 4,425,223 | 1/1984 | Miller | 208/48 AA |
| 4,444,649 | 4/1984 | Dvoracek | 208/48 AA |

Primary Examiner—D. E. Gantz
Assistant Examiner—Lance Johnson
Attorney, Agent, or Firm—John G. Premo; Robert A. Miller; Donald G. Epple

[57] ABSTRACT

An improved method of reducing fouling and corrosion in ethylene cracking furnaces using petroleum feedstocks, the improvement comprising treating the petroleum feedstock with at least 10 ppm of a compound chosen from the group consisting of phosphite esters, phosphate esters, thiophosphite esters, thiophosphate esters and mixtures thereof, said esters being characterized by the formulas:

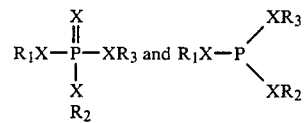

where X equals S or O, and $R_1$, $R_2$, and $R_3$, are each independently selected from the group consisting of hydrogen, water soluble amine, alkyl, aryl, alkaryl, cycloalkyl, alkenyl, and aralkyl group provided that in at least one and not more than two of each $R_1$, $R_2$, and $R_3$ are water soluble amines having partition coefficients greater than 1.0.

8 Claims, No Drawings

USE OF PHOSPHATE AND THIOPHOSPHATE ESTERS NEUTRALIZED WITH WATER SOLUBLE AMINES AS ETHYLENE FURNACE ANTI-COKING ANTIFOULANTS

This application is a continuation-in-part of abandoned Ser. No. 522,292 filed Aug. 11, 1983, which in turn is a continuation-in-part of copending Ser. No. 410,218 filed Aug. 23, 1982 now abandoned.

PRIOR ART

It would be noted that U.S. Pat. No. 4,105,540 discloses the use of the specific compounds described and claimed in this specification. There is no showing, however, in the patent that these materials have specific anticorrosive properties.

INTRODUCTION

Weinland, U.S. Pat. No. 4,105,540, incorporated by reference herein, teaches the use of phosphorus containing compounds as anti-foulants in ethylene cracking furnaces.

Specifically, this Weinland patent, teaches that phosphate and phosphite mono and diesters in small amounts function as anti-foulant additives in ethylene cracking furnaces which are subjected to elevated temperatures from about 500°–1,700° F. These furnaces produce material that deposits and accumulates upon furnace surfaces including furnace coils and transfer line exchangers and fouls these surfaces leading inevitably to plant shut down and expensive maintenance. The antifoulants of the Weinland patent inhibit and suppress this fouling and also help to clean up previously fouled furnace surfaces.

In accordance with U.S. Pat. No. 4,105,540, the invention is generally described as follows:

"This invention entails an improved process for reducing the fouling tendencies experienced in ethylene cracking furnaces including the formation of coking and polymer deposition on furnace coils and transfer line exchangers. The treatment is effective over the temperature range 500°–1,700° F. which are found in ethylene cracking furnaces.

"The method involves treatment of feed stock with at least 10 ppm and, preferably 25–100 ppm of the phosphorus ester antifoulants described below. In addition, it is preferred that plant equipment surfaces be pretreated with these compounds in the absence of the feed stock. The phosphate ester compounds employed in this invention are characterized by the general formula:

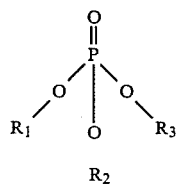

where $R_1$, $R_2$, and $R_3$ are each individually selected from the group consisting of hydrogen, addition complexes of hydrogen with amines, alkyl, aryl, alkaryl and cycloalklyl, alkenyl, and aralkyl, and provided that in any given such phosphate ester at least one and not more than two of each of $R_1$, $R_2$, and $R_3$ are hydrogen or an addition complex of hydrogen with an amine.

"The phosphite ester compounds employed in this invention are characterized by the general formula:

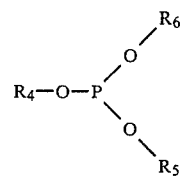

where $R_4$, $R_5$, and $R_6$ are each individually selected from the group consisting of hydrogen, addition complexes of hydrogen with amines, alkyl, aryl, alkaryl and cycloalkyl, alkenyl, and provided that in any given such phosphite ester at least one and not more than two of each of $R_1$, $R_2$, and $R_3$ are hydrogen or an addition complex of hydrogen with an amine."

"The preferred amine neutralized phosphate and phosphite mono and di esters are neutralized with fatty amines with a preferred amine being the material Primene 81-R, which is described in U.S. Pat. No. 4,105,540 as follows:

"The primary constituent of 'Primene 81-R' is reported to be:

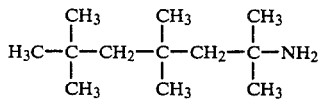

"The primary constituent of 'Primene JM-T' is reported to be essentially the same structure as 'Primene 81-R', but with 22 carbons. 'Primene' is a trademark of the Rohm & Haas Company for its brand of tertiary alkyl primary amines."

Experience has shown that the phosphate and phosphite esters described above which have been neutralized with fatty amines such as Primene 81-R when used over prolonged periods of time in ethylene furnaces while providing antifouling protection do not provide corrosion protection.

It would be benefit if it were possible to provide antifoulant compositions having effectiveness of those described in U.S. Pat. No. 4,105,540 yet would also provide corrosion protection when used over prolonged periods of time.

THE INVENTION

The invention is an improved method of reducing fouling and corrosion in ethylene cracking furnaces using petroleum feedstocks, the improvement which comprises treating the petroleum feedstock with at least 10 ppm and preferably 25–500 ppm of a compound chosen from the group consisting of phosphite esters, phosphate esters, thiophosphite esters, thiophosphate esters and mixtures thereof, said esters being represented by Formulas I and II below:

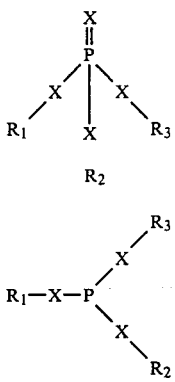

FORMULA I

FORMULA II

In the above formulas, X equals S or O, and $R_1$, $R_2$, and $R_3$ are each independently selected from the group consisting of hydrogen, water soluble amine, alkyl, aryl, alkaryl, cycloalkyl, alkenyl, and arylalkyl radical provided that at least one and no more than two of each of $R_1$, $R_2$, and $R_3$ are water soluble amines, and at least one of each $R_1$, $R_2$, and $R_3$ is selected from the group consisting of alkyl, aryl, alkaryl, cycloalkyl, alkenyl, and arylalkyl. When the term water soluble amine is used herein and in the claims, it means the water soluble amine salt group.

THE WATER SOLUBLE AMINES

The water soluble amines useful in this invention have partition coefficients greater than or equal to 1.0. As shown in the list below, Primene 81-R, the preferred amine in the Weinland patent, is not water soluble as exemplified by its partition coefficient which is several orders of magnitude smaller than the other water soluble amines listed.

Water soluble amines having partition coefficients greater than 1.0 include the following:

TABLE I

| PARTITION COEFFICIENTS OF NEUTRALIZING AMINES | |
| --- | --- |
| AMINE | PARTITION COEFFICIENT ($K_p$) |
| Ethylene Diamine | 1,060 |
| Monoethanolamine | 180 |
| Morpholine | 51 |
| Methoxypropylamine | 46 |
| n-Propylamine | 3.2 |
| Piperidine | 1.2 |
| Primene 81-R | 0.0006 |

Other water soluble amines having partition coefficients greater than 1.0 useful in the practice of this invention include: ethylamine, isopropylamine, N-methyl morpholine, aminoethyl ethanolamine, diethanolamine, diethylethanolamine, dimethyl ethanolamine, N-hydroxy ethyl morpholine, N-methyldiethanolamine, triethanolamine, 1,1-dihydroxymethylethylamine, 1,1-dihydroxymethyl-n-propylamine, pyrrolidone, 5-methyl-2-oxazolidone, 2-oxazolidone, imidazole, pyridine, N,N-dimethyl propanediamine, propanolamine, and ethoxypropylamine In the above description and in Table I above, partition coefficients were determined as follows:
1. Add 5.0 gm of the amine to be tested to a 4 oz. bottle containing 50 ml of distilled water and 50 ml of $C_7$ hydrocarbon. Cap and shake vigorously for one minute.
2. Place bottles horizontally on mechanical shaker for 20 minutes.
3. Remove bottles from shaker and allow phases to separate. Let stand for 1½ hours.
4. Determine the amine concentration in both the aqueous and hydrocarbon phases by titrating an aliquot of each phase with alcoholic HCl to a methyl orange end point.
5. Record the partition coefficient ($K_p$) of the amine between distilled water and $C_7$ hydrocarbon under the conditions of this test.

$$K_p = \frac{\text{amine concentration in aqueous phase}}{\text{amine concentration in hydrocarbon phase}}$$

While the above description is illustrative of the amines intended for use in this invention, it is in no way complete. Other amines having partition coefficients greater than 1.0 will perform in this invention.

Specific examples of compounds falling under the above formulas and which represent preferred species of the invention are the water soluble amine, and particularly the morpholine salts of:

(1) a blend of the mono and di isooctylthiophosphate ester;

(2) a blend of the mono and di isooctylphosphate ester; and (3) di n-butylphosphite.

A more detailed description of these compounds and their methods of manufacture are disclosed in U.S. Pat. No. 4,105,540, which has previously been incorporated herein by reference.

To illustrate the advantages of the invention, the following are presented by way of Examples.

EXAMPLE 1

A commercial ethylene plant was treated with a commercial organo phosphorus material of the type described in U.S. Pat. No. 4,105,540. This material was neutralized with Primene 81-R. The primary constituent of Primene 81-R is reported to be

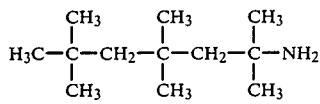

The treatment successfully prevented fouling of the furnace coils and transfer line exchangers. After several months had passed, however, evidence of corrosion was observed.

EXAMPLE 2

In order to show the benefit of the instant invention, morpholine neutralized phosphate and thiophosphate ester materials were tested.

The experimental procedure consisted of placing the compound to be tested along with water and a heavy aromatic naphtha into a laboratory autoclave. The mixture was then heated to 160° C. and held at that temperature for 6 hours.

Using the above experimental technique, the following morpholine salts were compared against the following similar Primene 81-R neutralized commercial products of the Weinland patent:

(1) a blend of the mono and di isooctylthiophosphate ester;

(2) a blend of the mono and di isooctylphosphate ester; and (3) di n-butylphosphite.

In all instances, the water soluble amine neutralized compositions of this invention substantially reduced corrosion, which corrosion was evidenced when the Weinland products (Primene 81-R neutralized) were run.

EXAMPLE 3

A commercial ethylene cracking furnace was being fed an ethane/propane mixture. The Primene 81-R neutralized thiophosphate ester of Formula I below was injected into the main hydrocarbon feed line before dilution steam addition at 100 ppm based on hydrocarbon feed. After 101 operating days (2,424 process hours), a leak due to localized corrosion developed in a portion of the A 335-GRP-11 1¼ chrome ½ molybdenum steel convection section coil immediately downstream of the point where dilution steam was added. The corroded tube section of the above steel was replaced by an identical steel section, and the furnace antifoulant program was continued unchanged.

After 137 operating days (3,288 process hours), a leak due to localized corrosion developed again in the same place on the new section of coil. This section was again replaced.

The product used in the antifoulant program was then changed. The morpholine neutralized thiophosphate ester of Formula II was injected at the same location at 100 ppm. As of Mar. 28, 1983, there had been 132 operating days (3,168 process hours) with this new antifoulant. No leaks had developed. An ultrasonic scan after approximately 80 process days (1,920 process hours) showed no evidence of corrosion.

FORMULA I

Primene 81-R neutralized product:

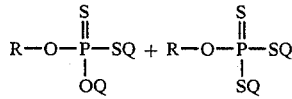

Neutralized 1:1 mole ratio (amine:ester) wherein:
R is iso $C_8$
Q is hydrogen or a hydrogen complex of "Primene 81-R" with the proviso that at least one occurance of Q is "Primene 81-R".

FORMULA II

Morpholine neutralized product:

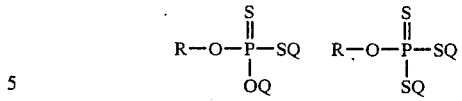

Neutralized 2:1 mole ratio (amine:ester) wherein:
R is iso $C_8$
Q is hydrogen or morpholine with the proviso that at least one occurance of Q is morpholine.

I claim:

1. An improved method of reducing fouling and corrosion in ethylene cracking furnaces using petroleum feedstocks, the improvement comprising admixing the petroleum feedstock with at least 10 ppm of a compound chosen from the group consisting of phosphite esters, phosphate esters, thiophosphite esters, thiophosphate esters and mixtures thereof, said esters being characterized by the formulas:

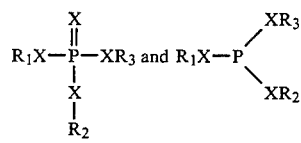

where X equals S or O, and $R_1$, $R_2$, and $R_3$, are each independently selected from the group consisting of hydrogen, water soluble amine, alkyl, aryl, alkaryl, cycloaklyl, alkenyl, and arylalkyl group provided that in at least one and not more than two of each $R_1$, $R_2$, and $R_3$ are water soluble amines having partition coefficients greater than about 3.0 and at least one of $R_1$, $R_2$, and $R_3$ is selected from the group consisting of alkyl, aryl, alkaryl, cycloaklyl, alkenyl, and arylalkyl.

2. The method of claim 1 wherein the ester is a blend of the mono and di isooctylthiophosphate ester.

3. The method of claim 1 wherein the ester is a blend of the mono and di isooctylphosphate ester.

4. The method of claim 1 wherein the ester is di n-butylphosphite.

5. The method of claim 1 wherein the water soluble amine is morpholine.

6. The method of claim 2 wherein the water soluble amine is morpholine.

7. The method of claim 3 wherein the water soluble amine is morpholine.

8. The method of claim 1 wherein the water soluble amine is selected from the group consisting of:
Morpholine,
Ethylene Diamine,
Monoethanolamine, and
Methoxypropylamine.

* * * * *